(12) United States Patent
Harmeyer

(10) Patent No.: US 11,457,848 B2
(45) Date of Patent: Oct. 4, 2022

(54) SYSTEM AND METHOD FOR DETERMINING INCONTINENCE DEVICE REPLACEMENT INTERVAL

(71) Applicant: Hill-Rom Services, Inc., Batesville, IN (US)

(72) Inventor: John V. Harmeyer, Cleves, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 114 days.

(21) Appl. No.: 16/862,782

(22) Filed: Apr. 30, 2020

(65) Prior Publication Data

US 2020/0253528 A1  Aug. 13, 2020

Related U.S. Application Data

(63) Continuation of application No. 15/822,337, filed on Nov. 27, 2017, now abandoned.

(60) Provisional application No. 62/427,398, filed on Nov. 29, 2016.

(51) Int. Cl.
| | |
|---|---|
| *A61B 5/20* | (2006.01) |
| *A61B 5/00* | (2006.01) |
| *A61B 5/11* | (2006.01) |
| *A61F 13/42* | (2006.01) |
| *A61B 5/318* | (2021.01) |
| *A61B 5/369* | (2021.01) |
| *A61B 5/0205* | (2006.01) |

(52) U.S. Cl.
CPC ............ *A61B 5/202* (2013.01); *A61B 5/11* (2013.01); *A61B 5/1118* (2013.01); *A61B 5/208* (2013.01); *A61B 5/318* (2021.01); *A61B 5/369* (2021.01); *A61B 5/4809* (2013.01); *A61B 5/6892* (2013.01); *A61F 13/42* (2013.01); *A61B 5/0205* (2013.01); *A61B 2562/029* (2013.01); *A61B 2562/0252* (2013.01); *A61B 2562/046* (2013.01)

(58) Field of Classification Search
CPC ....... A61B 5/202; A61B 5/208; A61B 5/0205; A61B 5/1118; A61B 5/4809; A61B 5/6892
See application file for complete search history.

(56) References Cited

U.S. PATENT DOCUMENTS

| | | | |
|---|---|---|---|
| 1,772,232 A | 8/1930 | Van Guilder |
| 2,127,538 A | 8/1938 | Seiger |
| 2,644,050 A | 6/1953 | Wright |
| 2,668,202 A | 2/1954 | Kaplan |
| 2,726,294 A | 12/1955 | Kroening et al. |

(Continued)

FOREIGN PATENT DOCUMENTS

| | | |
|---|---|---|
| CN | 102568259 A | 7/2012 |
| CN | 102985853 A | 3/2013 |

(Continued)

*Primary Examiner* — Eric D. Bertram
(74) *Attorney, Agent, or Firm* — Barnes & Thornburg LLP

(57) ABSTRACT

A method of providing hygiene services to a patient. The method includes acquiring patient status data of a patient with a sensor. Incontinence event data is acquired with an incontinence detection system. After the occurrence of the incontinence event, a sleep status of the patient is determined based the patient status data. A time period to provide hygiene services to the patient is determined based on the incontinence event data and the sleep status of the patient.

25 Claims, 11 Drawing Sheets

| INCONTINENCE TYPE | INCONTINENCE AMOUNT | SLEEP STATE | CHANGING RECOMMENDATION |
|---|---|---|---|
| FECAL | ANY | ANY | ASAP |
| URINE | 0ML-10ML | ANY | NO CHANGE |
| URINE | 10ML-20ML | ANY | 1-2 HOURS |
| URINE | 20ML-40ML | LESS THAN 4 HOURS | 1-2 HOURS |
| URINE | 20ML-40ML | 4-6 HOURS | 30-60 MINUTES |
| URINE | 20ML-40ML | GREATER THAN 6 HOURS | ASAP |
| URINE | 60ML-80ML | LESS THAN 4 HOURS | 30-60 MINUTES |
| URINE | 60ML-80ML | GREATER THAN 4 HOURS | ASAP |
| URINE | 80+ML | ANY | ASAP |

(columns 556 / 568 / 572 bracket INCONTINENCE AMOUNT, SLEEP STATE, and CHANGING RECOMMENDATION respectively)

(56) References Cited

U.S. PATENT DOCUMENTS

| | | |
|---|---|---|
| 2,907,841 A | 10/1959 | Campbell |
| 3,199,095 A | 8/1965 | Hiroo |
| 3,696,357 A | 10/1972 | Kilgore |
| 3,971,371 A | 7/1976 | Bloom |
| 4,001,531 A | 1/1977 | Crockett |
| 4,069,817 A | 1/1978 | Fenole et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Roberts |
| 4,347,503 A | 8/1982 | Uyehara |
| 4,539,559 A | 9/1985 | Kelly et al. |
| 4,965,554 A | 10/1990 | Darling |
| 5,081,422 A | 1/1992 | Shih |
| 5,086,294 A | 2/1992 | Kasegi |
| 5,137,033 A | 8/1992 | Norton |
| 5,144,284 A | 9/1992 | Hammett |
| 5,291,181 A | 3/1994 | Deponte |
| 5,438,721 A | 8/1995 | Pahno et al. |
| 5,459,452 A | 10/1995 | Deponte |
| 5,491,609 A | 2/1996 | Dankman et al. |
| 5,537,095 A | 7/1996 | Dick et al. |
| 5,570,082 A | 10/1996 | Mahgerefteh et al. |
| 5,675,854 A | 10/1997 | Zibelin |
| 5,760,694 A | 6/1998 | Nissim et al. |
| 5,790,035 A | 8/1998 | Ho |
| 5,824,883 A | 10/1998 | Park et al. |
| 5,910,080 A | 6/1999 | Selton |
| 5,947,943 A | 9/1999 | Lee |
| 6,028,241 A | 2/2000 | Armstead |
| 6,047,419 A | 4/2000 | Ferguson |
| 6,104,311 A | 8/2000 | Lastinger |
| 6,292,102 B1 | 9/2001 | Smith |
| 6,341,393 B1 | 1/2002 | Votel |
| 6,351,215 B2 | 2/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,559,772 B2 | 5/2003 | Zand et al. |
| 6,583,722 B2 | 6/2003 | Jeutter et al. |
| 6,603,403 B2 | 8/2003 | Jeutter et al. |
| 6,639,517 B1 | 10/2003 | Chapman et al. |
| 6,832,507 B1 | 12/2004 | Van De Berg et al. |
| 6,933,849 B2 | 8/2005 | Sawyer |
| 6,948,205 B2 | 9/2005 | Van Der Wurf et al. |
| 7,017,213 B2 | 3/2006 | Chisari |
| 7,053,524 B2 | 5/2006 | Edmonson et al. |
| 7,071,830 B2 | 7/2006 | Sahlberg et al. |
| 7,120,952 B1 | 10/2006 | Bass et al. |
| 7,141,715 B2 | 11/2006 | Shapira |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,348,930 B2 | 3/2008 | Lastinger et al. |
| 7,355,090 B2 | 4/2008 | Ales, III et al. |
| 7,489,252 B2 | 2/2009 | Long et al. |
| 7,498,478 B2 | 3/2009 | Long et al. |
| 7,595,734 B2 | 9/2009 | Long et al. |
| 7,595,743 B1 | 9/2009 | Winger et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,633,378 B2 | 12/2009 | Rogers et al. |
| 7,649,125 B2 | 1/2010 | Ales, III et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,834,234 B2 | 11/2010 | Roe et al. |
| 7,834,235 B2 | 11/2010 | Long et al. |
| 7,849,544 B2 | 12/2010 | Flocard et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,237,572 B2 | 8/2012 | Clement et al. |
| 8,428,605 B2 | 4/2013 | Pedersen et al. |
| 8,471,715 B2 | 6/2013 | Solazzo et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,826,473 B2 | 9/2014 | Flanagan et al. |
| 8,878,557 B2 | 11/2014 | Kristiansen et al. |
| 8,878,676 B2 | 11/2014 | Koblasz |
| 8,914,923 B2 | 12/2014 | Smith |
| 8,933,292 B2 | 1/2015 | Abraham et al. |
| 9,165,449 B2 * | 10/2015 | Ribble ............... A61G 7/05769 |
| 9,322,797 B1 | 4/2016 | Lastinger et al. |
| 9,366,644 B1 | 6/2016 | Lastinger et al. |
| 9,506,886 B1 | 11/2016 | Woodbury et al. |
| 9,649,230 B1 | 5/2017 | Li |
| 9,681,996 B2 | 6/2017 | Prioleau et al. |
| 9,806,886 B2 | 10/2017 | Rajsic |
| 10,022,277 B2 | 7/2018 | Heil et al. |
| 10,115,291 B2 | 10/2018 | Tallent et al. |
| 10,143,608 B2 | 12/2018 | Kostic |
| 10,159,607 B2 | 12/2018 | Voll et al. |
| 10,251,793 B1 | 4/2019 | Li |
| 10,299,968 B2 | 5/2019 | Heil et al. |
| 10,322,036 B2 | 6/2019 | Haire et al. |
| 10,458,876 B1 | 6/2019 | Billman et al. |
| 10,347,114 B2 | 7/2019 | Johnson et al. |
| 10,349,881 B1 | 7/2019 | Monson et al. |
| 10,371,558 B2 | 8/2019 | Tevs et al. |
| 10,420,682 B2 | 9/2019 | Lindstrm et al. |
| 10,422,742 B2 | 9/2019 | Safai et al. |
| 10,470,689 B2 | 11/2019 | Kilcran et al. |
| 10,481,105 B2 | 11/2019 | Advani et al. |
| 10,489,661 B1 | 11/2019 | Rush et al. |
| 10,527,487 B2 | 1/2020 | Pretorius et al. |
| 10,548,476 B2 | 2/2020 | Lane et al. |
| 10,600,204 B1 | 3/2020 | Rush et al. |
| 10,624,587 B2 | 4/2020 | Baker et al. |
| 10,653,567 B2 | 5/2020 | Weidman et al. |
| 10,656,081 B2 | 5/2020 | Safai et al. |
| 10,863,672 B2 | 12/2020 | Todd et al. |
| 10,871,458 B2 | 12/2020 | Todd et al. |
| 10,945,892 B2 | 3/2021 | Severns |
| 10,970,991 B1 | 4/2021 | Alovert |
| 11,039,530 B2 | 6/2021 | Hanazawa |
| 11,083,636 B2 | 8/2021 | Potter et al. |
| 11,147,490 B2 | 10/2021 | Stevens et al. |
| 11,173,073 B2 | 11/2021 | Macnaughton et al. |
| 11,197,785 B2 | 12/2021 | Mehta et al. |
| 11,278,457 B2 | 3/2022 | Benz et al. |
| 11,311,436 B2 | 4/2022 | Corbin et al. |
| 2002/0145526 A1 | 10/2002 | Friedman et al. |
| 2005/0003865 A1 | 1/2005 | Lastinger et al. |
| 2005/0060246 A1 | 3/2005 | Lastinger et al. |
| 2005/0174246 A1 | 8/2005 | Picco et al. |
| 2005/0242946 A1 | 11/2005 | Hubbard et al. |
| 2005/0245839 A1 * | 11/2005 | Stivoric ............. A61B 10/0012 |
| | | 374/E1.004 |
| 2005/0277441 A1 | 12/2005 | Lastinger et al. |
| 2006/0114754 A1 * | 6/2006 | MacDonald ............... G04F 1/00 |
| | | 368/327 |
| 2006/0164320 A1 | 7/2006 | Lastinger et al. |
| 2006/0270351 A1 | 11/2006 | Lastinger et al. |
| 2007/0159332 A1 | 7/2007 | Koblasz |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson et al. |
| 2009/0160648 A1 | 6/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0145294 A1 | 6/2010 | Song et al. |

(56) References Cited

U.S. PATENT DOCUMENTS

| | | |
|---|---|---|
| 2011/0025458 A1 | 2/2011 | Rokhsaz et al. |
| 2011/0092890 A1 | 4/2011 | Stryker et al. |
| 2011/0095884 A1 | 4/2011 | Xu et al. |
| 2011/0115635 A1 | 5/2011 | Petrovski et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2012/0092027 A1 | 4/2012 | Forster |
| 2012/0130330 A1 | 5/2012 | Wilson et al. |
| 2012/0157947 A1 | 6/2012 | Nhan et al. |
| 2012/0217311 A1 | 8/2012 | Rokhsaz et al. |
| 2013/0079590 A1 | 3/2013 | Bengtson |
| 2013/0109929 A1 | 5/2013 | Menzel |
| 2013/0123726 A1 | 5/2013 | Yu et al. |
| 2014/0148772 A1 | 5/2014 | Hu et al. |
| 2014/0200538 A1 | 7/2014 | Euliano et al. |
| 2014/0236629 A1 | 8/2014 | Kim et al. |
| 2014/0247125 A1 | 9/2014 | Barsky |
| 2014/0266735 A1 | 9/2014 | Riggio et al. |
| 2014/0358099 A1 | 12/2014 | Durgin et al. |
| 2015/0080819 A1 | 3/2015 | Charna et al. |
| 2015/0080834 A1 | 3/2015 | Mills |
| 2015/0087935 A1 | 3/2015 | Davis et al. |
| 2015/0109442 A1* | 4/2015 | Derenne .............. G16H 40/67 348/143 |
| 2015/0294549 A1* | 10/2015 | Ribble ................ G16H 40/60 340/573.5 |
| 2016/0174892 A1 | 6/2016 | Benson et al. |
| 2017/0112681 A1 | 4/2017 | Mancini et al. |
| 2017/0156594 A1* | 6/2017 | Stivoric ............ A61B 5/14532 |
| 2017/0236398 A1 | 8/2017 | Eddy et al. |
| 2018/0014981 A1 | 1/2018 | Schiavenato et al. |
| 2018/0333306 A1* | 11/2018 | Ahong ................ A61B 5/6843 |
| 2019/0192066 A1 | 6/2019 | Schoess et al. |
| 2019/0307405 A1 | 10/2019 | Meyerson et al. |
| 2020/0175836 A1 | 6/2020 | Rogers et al. |
| 2020/0330021 A1 | 10/2020 | Samadani |
| 2021/0093244 A1 | 4/2021 | Monson et al. |

FOREIGN PATENT DOCUMENTS

| | | |
|---|---|---|
| CN | 107923815 A | 4/2018 |
| CN | 104970921 B | 7/2019 |
| CN | 107530214 B | 1/2021 |
| DE | 4137631 A1 | 5/1992 |
| DE | 102007050074 A1 | 4/2009 |
| DE | 102017125323 A1 | 5/2019 |
| EP | 335279 A1 | 10/1989 |
| EP | 2014267 A1 | 1/2009 |
| EP | 2019659 A1 | 2/2009 |
| EP | 2444039 A1 | 4/2012 |
| EP | 2452183 A1 | 5/2012 |
| EP | 2496197 A1 | 9/2012 |
| EP | 2582341 A1 | 4/2013 |
| EP | 1906794 A4 | 5/2014 |
| EP | 2729107 A1 | 5/2014 |
| EP | 2739254 A1 | 6/2014 |
| EP | 3611668 A1 | 2/2020 |
| EP | 3544506 A4 | 7/2020 |
| EP | 3721808 A1 | 10/2020 |
| EP | 3189823 B1 | 12/2020 |
| EP | 3598782 B1 | 4/2021 |
| EP | 3403580 B1 | 5/2021 |
| EP | 3879459 A1 | 9/2021 |
| FR | 3099044 A1 | 1/2021 |
| GB | 2145859 A | 4/1985 |
| GB | 2408204 A | 5/2005 |
| SE | 534533 C2 | 9/2011 |
| TW | M514624 U | 12/2015 |
| WO | 8910110 A1 | 11/1989 |
| WO | 9420002 A1 | 9/1994 |
| WO | 0125817 A2 | 4/2001 |
| WO | 02103645 A2 | 12/2002 |
| WO | 2006108540 A1 | 10/2006 |
| WO | 2007069968 A1 | 6/2007 |
| WO | 2008130298 A1 | 10/2008 |
| WO | 2010043368 A1 | 4/2010 |
| WO | 2011107580 A1 | 9/2011 |
| WO | 2012136157 A1 | 10/2012 |
| WO | 2014165041 A2 | 10/2014 |
| WO | 2015137999 A1 | 9/2015 |
| WO | 2021138459 A1 | 7/2021 |

* cited by examiner

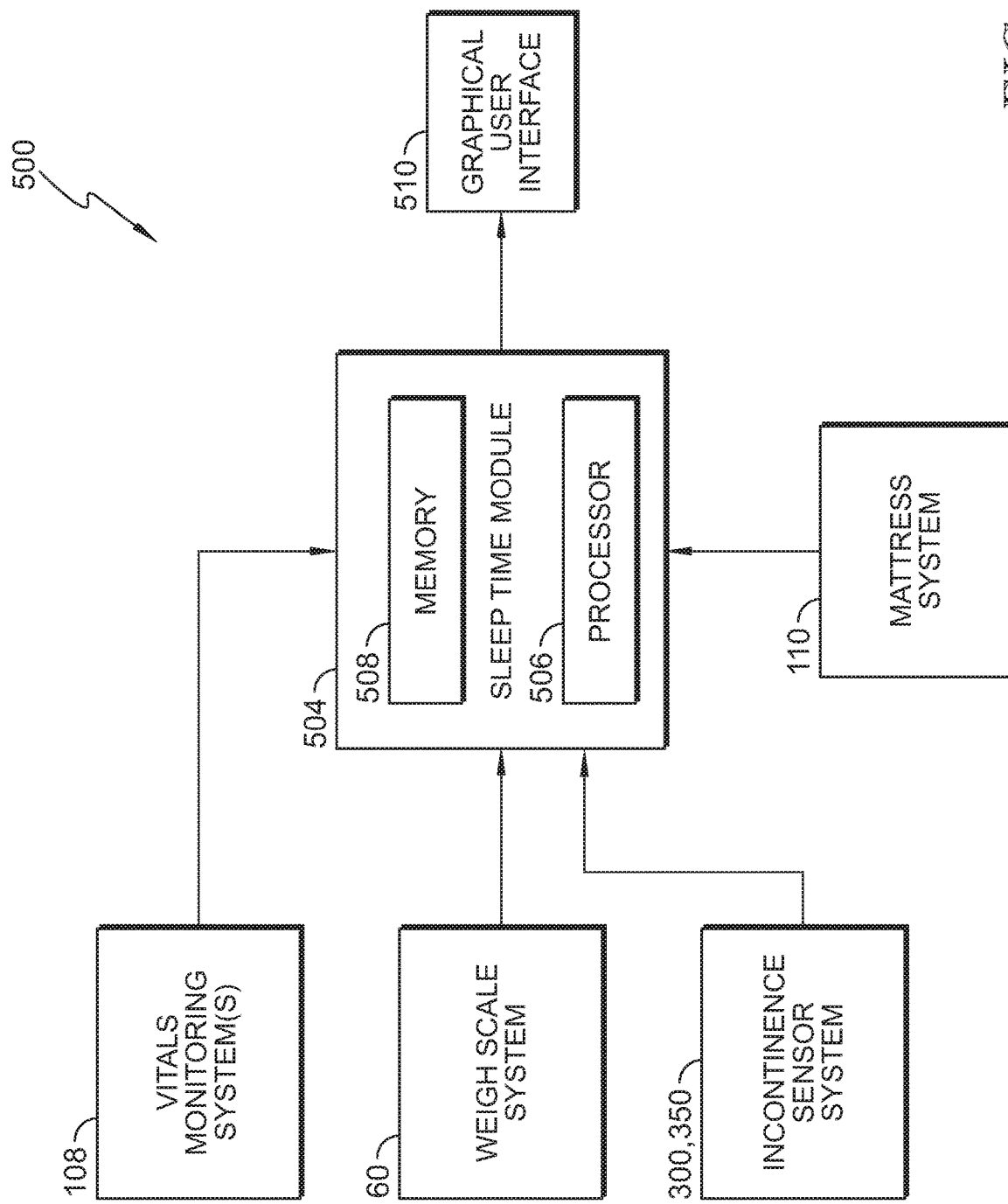

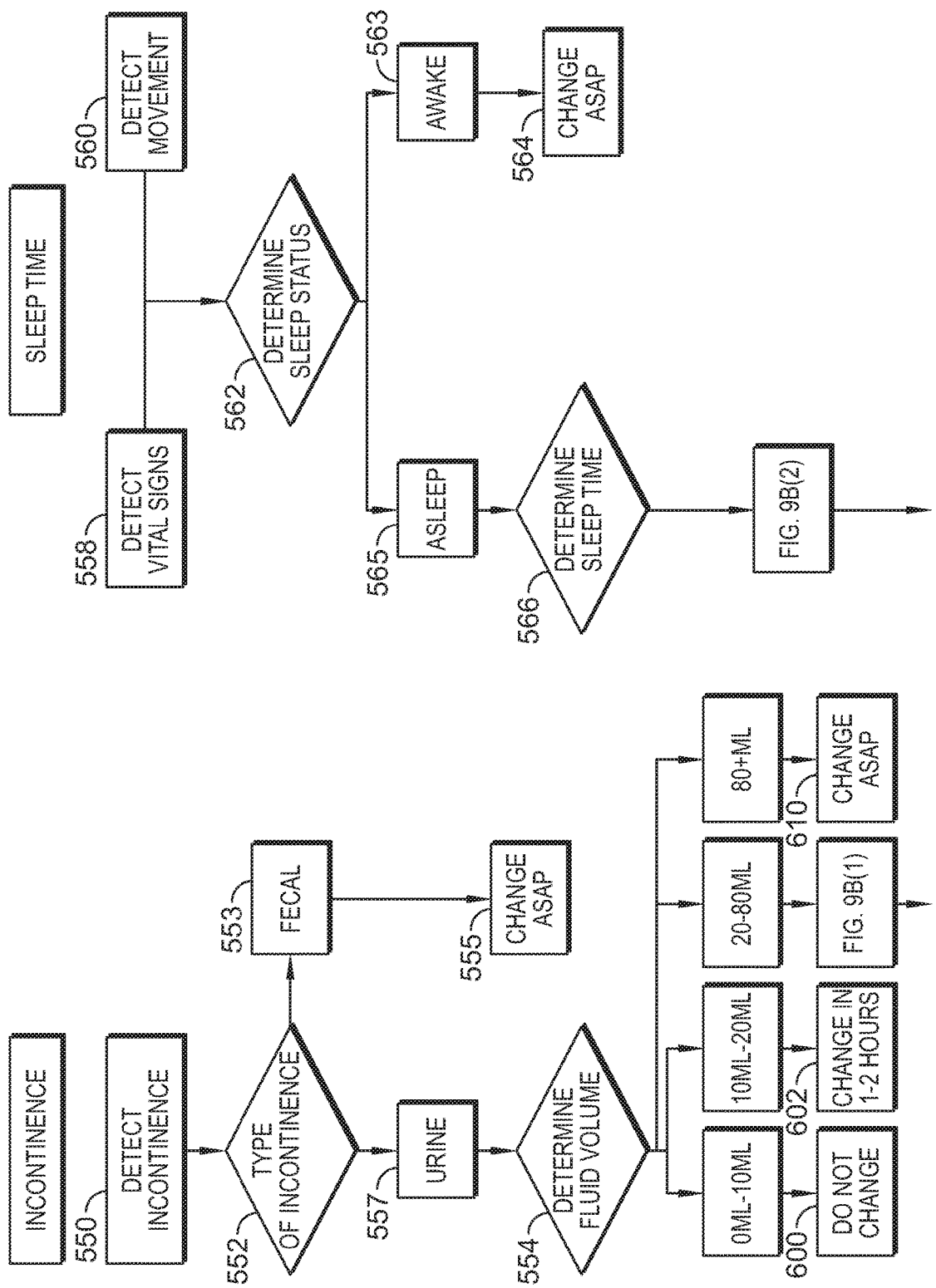

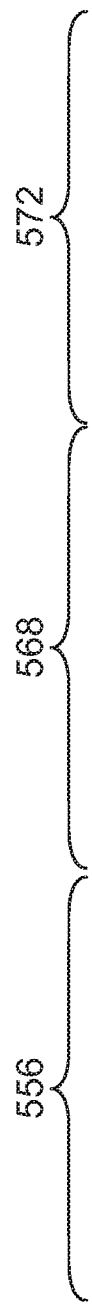

SYSTEM AND METHOD FOR DETERMINING INCONTINENCE DEVICE REPLACEMENT INTERVAL

CROSS-REFERENCE TO RELATED APPLICATIONS

The present application is a continuation of U.S. application Ser. No. 15/822,337, filed Nov. 27, 2017, which claims the benefit, under 35 U.S.C. § 119(e) to U.S. Provisional Application Ser. No. 62/427,398, filed Nov. 29, 2016, which is hereby incorporated by reference herein.

BACKGROUND

The present disclosure relates to incontinence detection systems and particularly, to incontinence detection systems that use a pad beneath a patient lying in a hospital bed or garment secured to the patient. More particularly, the present disclosure relates to a method of providing hygiene services to a patient by determining incontinence device replacement intervals.

Good medical practice dictates that patients who are incontinent should be removed from the wet environment as soon as possible to avoid skin breakdown which can potentially lead to pressure ulcers. Incontinence detection systems alert caregivers to the occurrence of an incontinent event so that hygiene services can be provided as quickly as possible. Hygiene services may include changing patient linens, changing patient garments, and/or moving the patient to a clean hospital bed. However, many patients experience difficulty sleeping in a hospital bed. As a result, it may not be advantageous to provide hygiene services immediately after the occurrence of an incontinent event. Particularly, if a patient experiences an incontinent event while sleeping, the caregiver may not want to wake the patient to provide hygiene services.

SUMMARY

The present application discloses one or more of the features recited in the appended claims and/or the following features which, alone or in any combination, may comprise patentable subject matter:

According to a first aspect of the present disclosure, a method of providing hygiene services to a patient is provided. The method includes acquiring patient status data of a patient with a sensor, and acquiring incontinence event data with an incontinence detection system. After the occurrence of the incontinence event, the method includes determining a sleep status of the patient based the patient status data. A time period to provide hygiene services to the patient is determined based on the incontinence event data and the sleep status of the patient.

In one embodiment, the method includes at least one of detecting an incontinence event and measuring a fluid volume of the incontinence event. Incontinence event data may be acquired with an incontinence detection system that includes a sensor pad including a plurality of electrically conductive traces. The presence of at least one of urine or fecal matter may be detected, wherein, after detecting fecal matter, the time period to provide hygiene services is as soon as possible. Alternatively, after detecting urine, the method may include determining whether the patient is asleep or awake, wherein, if the patient is awake, the time period to provide hygiene services is as soon as possible.

In one embodiment, the method includes measuring at least one vital sign of the patient, for example measuring at least one of brain activity of the patient with an electroencephalogram and heart activity of the patient with an electrocardiogram.

In one embodiment, the method includes measuring movement of the patient. Movement of the patient may be measured with at least one pressure sensor. Movement of the patient may be measured with a load cell.

In one embodiment, hygiene services include at least one of changing the patient's linens, changing the patient's garments, and moving the patient to a clean hospital bed.

In one embodiment, the method includes at least one of monitoring the occurrence of at least one of non-rapid eye movement sleep and rapid eye movement sleep, determining a period of time that the patient has slept, and comparing a fluid volume of the incontinence event to the period of time that the patient has slept.

In one embodiment, if the patient is asleep and the fluid volume is within a range of approximately 0 ml to approximately 10 ml, hygiene services are not provided. In one embodiment, if the patient is asleep and the fluid volume is within a range of approximately 10 ml to approximately 20 ml, the time period to provide hygiene services is within a range of approximately 1 hour to approximately 2 hours. In one embodiment, if the patient has been asleep for less than approximately four hours and the fluid volume is within a range of approximately 20 ml to approximately 40 ml, the time period to provide hygiene services is within a range of approximately 1 hour to approximately 2 hours. In one embodiment, if the patient has been asleep for a range of approximately four hours to approximately six hours and the fluid volume is within a range of approximately 20 ml to approximately 40 ml, the time period to provide hygiene services is within a range of approximately 30 minutes to approximately 1 hour. In one embodiment, if the patient has been asleep for over approximately six hours and the fluid volume is within a range of approximately 20 ml to approximately 40 ml, the time period to provide hygiene services is as soon as possible. In one embodiment, if the patient has been asleep for less than approximately four hours and the fluid volume is within a range of approximately 60 ml to approximately 80 ml, the time period to provide hygiene services is approximately 30 minutes to approximately 1 hour. In one embodiment, if the patient has been asleep for over approximately four hours and the fluid volume is within a range of approximately 60 ml to approximately 80 ml, the time period to provide hygiene services is as soon as possible. In one embodiment, if the patient is asleep and the fluid volume is greater than approximately 80 ml, the time period to provide hygiene services is as soon as possible.

According to a second aspect of the present disclosure, a system for providing hygiene services to a patient is provided. The system includes a sensor configured to acquire patient status data of a patient and an incontinence detection system configured to acquire incontinence event data. The system also includes, a processor configured to, after the occurrence of the incontinence event, determine a sleep status of the patient based the patient status data. The processor is further configured to determine a time period to provide hygiene services to the patient based on the incontinence event data and the sleep status of the patient.

BRIEF DESCRIPTION OF THE DRAWINGS

The foregoing and other features of the various embodiments of the methods and apparatuses described herein will become more apparent from the following detailed description and the accompanying drawings in which:

FIG. 8 is a block diagram of a system that determines a hygiene services schedule for a patient;

FIG. 9A is a flowchart showing a method for determining a hygiene services schedule for a patient;

FIG. 10 is a chart showing a hygiene services schedule for a patient.

DETAILED DESCRIPTION

The present disclosure relates to systems and methods for detecting incontinence or other moisture caused events associated with a person being monitored. Thus, it should be appreciated that the systems described herein are able to detect biofluids such as blood, urine, fecal matter, interstitial fluid, saline, or any other fluid having a large concentration of ions that easily conduct electricity. The term "incontinence" as used herein is intended to cover all of these biofluids. The present disclosure further describes systems and methods for reporting detected incontinence events to hospital caregivers, a nurse call system, or an EMR (electronic medical record) system to allow patients to be quickly removed from the soiled environment. The present disclosure further describes a method of determining a patient hygiene schedule. It should be appreciated that the patient hygiene schedule determines an approximate time to provide hygiene services to the patient based on an approximate amount of incontinence and an approximate amount of time that the patient has been sleeping.

Figure 1:
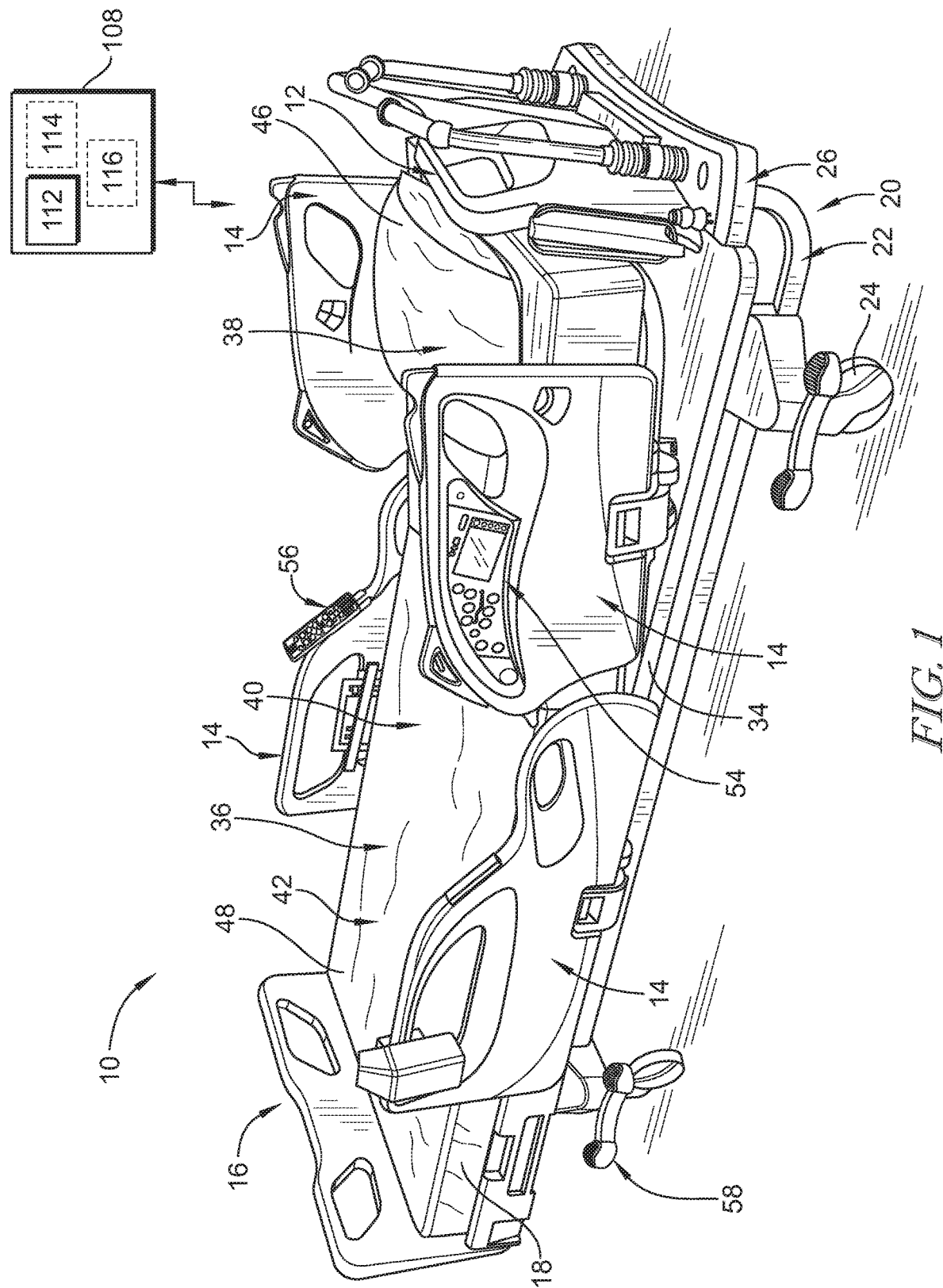
FIG. 1 is a perspective view from the head end on the patient's left of a patient support apparatus, wherein the patient support apparatus includes a vital signs monitoring system in communication therewith.

A patient support apparatus 10 embodied as a hospital bed is shown in FIG. 1. It will be appreciated that, although the present embodiments are described with respect to a hospital bed, the present embodiments may be utilized with any occupant support, for example, a hospital bed, a residential bed, a chair, a wheelchair, a mattress, a stretcher, a patient transport device, or any other type of person support apparatus. The patient support apparatus 10 has a fixed bed frame 20 which includes a stationary base frame 22 with casters 24 and an upper frame 26. The stationary base frame 22 is further coupled to a weigh frame 30 (shown in FIG. 3) that is mounted via frame member 32a and 32b (both shown in FIG. 3) to an adjustably positionable mattress support frame or deck 34 configured to support a mattress 18. The mattress 18 defines a patient support surface 36 which includes a head section 38, a seat section 40, and a foot section 42. The patient support apparatus 10 further includes a headboard 12 at a head end 46 of the patient support apparatus 10, a footboard 16 at a foot end 48 of the patient support apparatus 10, and a pair of siderails 14 coupled to the upper frame 26 of the patient support apparatus 10. The siderail 14 supports a patient monitoring control panel and/or a mattress position control panel 54 as shown in FIG. 1. The patient support apparatus 10 is generally configured to adjustably position the mattress support frame 34 relative to the base frame 22. Although the embodiment shows the control panel 54 supported on a siderail 14, the control panel 54 may be affixed to any portion of the patient support apparatus 10. In one embodiment, the control panel 54 may be configured as a remote that is either wirelessly coupled to or wired to the patient support apparatus 10.

Conventional structures and devices may be provided to adjustably position the mattress support frame 34, and such conventional structures and devices may include, for example, linkages, drives, and other movement members and devices coupled between base frame 22 and the weigh frame 30, and/or between weigh frame 30 and mattress support frame 34. The details of the structure of a suitable bed embodiment of a patient support apparatus may be found in application number PCT/US2016/034908 filed May 27, 2016 and titled "PATIENT SUPPORT APPARATUS", which is incorporated herein in its entirety. Control of the position of the mattress support frame 34 and mattress 18 relative to the base frame 22 or weigh frame 30 is provided, for example, by a patient control pendant 56, a mattress position control panel 54, and/or a number of mattress positioning pedals. The mattress support frame 34 may, for example, be adjustably positioned in a general incline from the head end 46 to the foot end 48 or vice versa. Additionally, the mattress support frame 34 may be adjustably positioned such that the head section 38 of the patient support surface 36 is positioned between minimum and maximum incline angles, e.g., 0-65 degrees, relative to horizontal or bed flat, and the mattress support frame 34 may also be adjustably positioned such that the seat section 40 of the patient support surface 36 is positioned between minimum and maximum bend angles, e.g., 0-35 degrees, relative to horizontal or bed flat. Those skilled in the art will recognize that the mattress support frame 34 or portions thereof may be adjustably positioned in other orientations, and such other orientations are contemplated by this disclosure and disclosed in the aforementioned application number PCT/US2016/034908.

The patient support apparatus 10 may be in communication with one or more vital signs monitoring systems 108. Although only one vital signs monitoring system 108 is shown in FIG. 1, the patient support apparatus 10 may include any number of vital signs monitoring systems 108. The vital signs monitoring system 108, as shown, is in wireless communication with the patient support apparatus 10. In other embodiments, the vital signs monitoring system 108 may be in wired communication with the patient support apparatus 10. The vital signs monitoring system 108 may activate or control electronically-controlled components associated with the patient support apparatus 10. As shown, the electronically-controlled components include an electrocardiogram 112. In one embodiment, the electronically-controlled components may also include at least one of an electroencephalogram 114 and/or a ventilator 116, among other things. In one embodiment, the electronically-controlled components may not include the electrocardiogram 112. It will be appreciated that any electronically-controlled components for monitoring vital signs may be incorporated into the vital signs monitoring system 108. In one embodiment, the electronically-controlled components may include any combination of electrocardiogram 112, electroencephalogram 114 and/or a ventilator 116, among other things. As discussed in detail below, the vital signs monitoring system 108 is configured to monitor various signals from the electronically-controlled components to receive and analyze vital sign data (e.g., to determine the brain activity, cardiac, respiratory, and/or snoring state of a patient, among other things).

Figure 2:
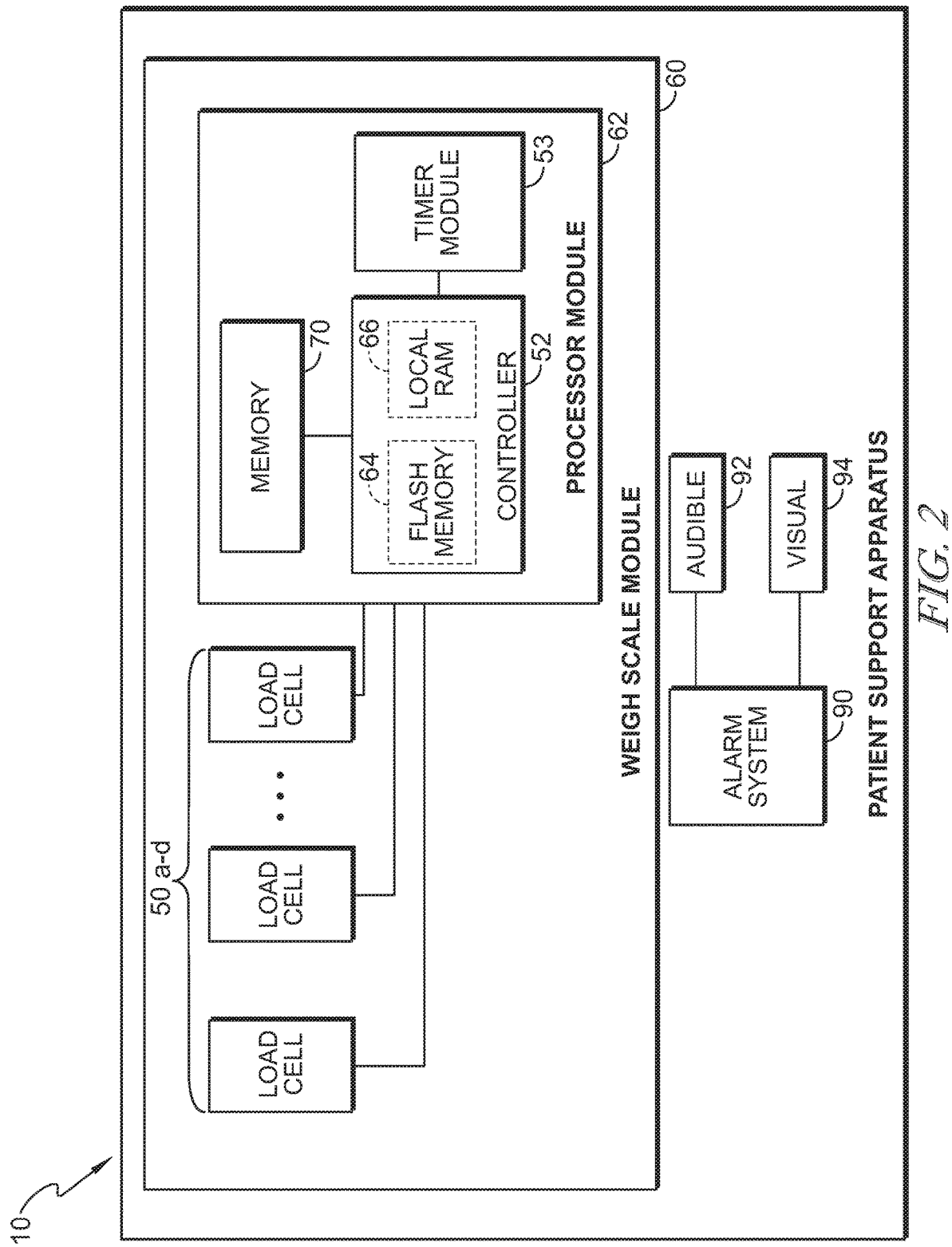
FIG. 2 is a block diagram of a portion of the electrical system of the patient support apparatus of FIG. 1 used to determine a tare weight of the patient support apparatus.

In one embodiment shown diagrammatically in FIG. 2, the patient support apparatus 10 includes a weigh scale system 60 and an alarm system 90, as disclosed in the aforementioned application number PCT/US2016/034908. The weight scale system 60 is configured to determine a plurality set of calibration weights for each of a number of load cells 50 for use in determining a location and an accurate weight of the patient. To determine a weight of a patient supported on the patient support surface 36, the load cells 50 are positioned between the weigh frame 30 and the base frame 22. Each load cell 50 is configured to produce a voltage or current signal indicative of a weight supported by that load cell 50 from the weigh frame 30 relative to the base frame 22. The weigh scale system 60 includes a processor 62 that is in communication with each of the respective load cells 50. The processor 62 includes a microprocessor-based controller 52 having a flash memory unit 64 and a local random-access memory (RAM) unit 66. The local RAM unit 66 is utilized by the controller 52 to temporarily store information corresponding to features and functions provided by the patient support apparatus 10. A memory 80 may store predetermined calibration positions 70, as described in FIG. 3. Additionally, a timer 53 may monitor the timing of weight displacement as measured by the weigh scale system 60. The alarm system 90 is configured to trigger an alarm if the movement of the patient exceeds a predetermined threshold. The alarm may be an audible alarm 92 and/or a visual alarm 94. The visual alarm 94 may be positioned, for example, on the mattress position control panel 54 and/or the patient control pendant 56.

Figure 3:
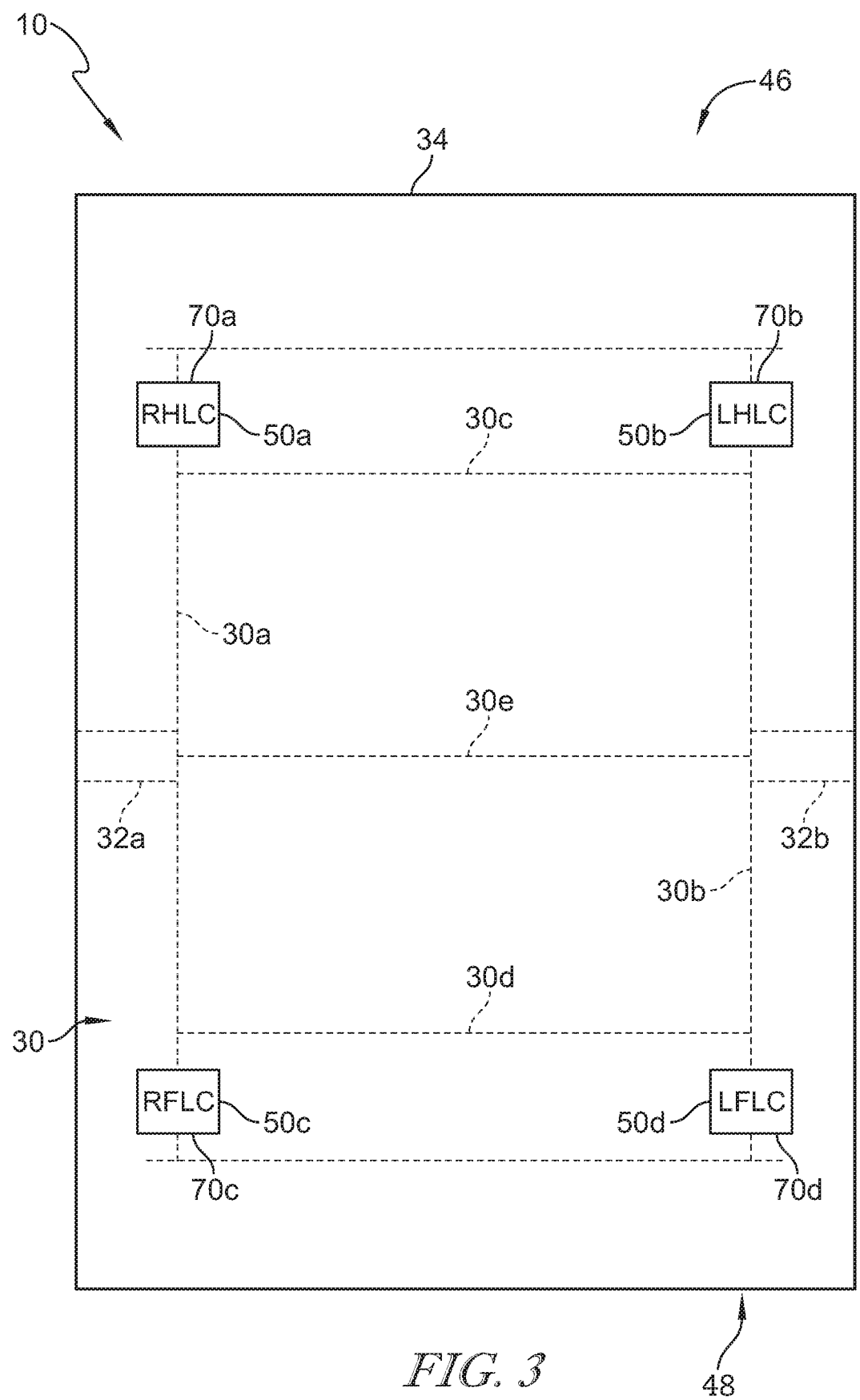
FIG. 3 is a diagrammatic representation of the positions of a number of load cells relative to the patient support apparatus of FIG. 1.

In the embodiment of FIG. 3, four such load cells 50a-50d are positioned between the weigh frame 30 and the base frame 22; one each near a different corner of the patient support apparatus 10. All four load cells 50a-50d are shown in FIG. 3. Some of the structural components of the patient support apparatus 10 will be designated hereinafter as "right", "left", "head" and "foot" from the reference point of an individual lying on the individual's back on the patient support surface 36 with the individual's head oriented toward the head end 46 of the patient support apparatus 10 and the individual's feet oriented toward the foot end 48 of the patient support apparatus 10. For example, the weigh frame 30 shown in FIG. 3 includes a head end frame member 30c mounted at one end to one end of a right side weigh frame member 30a and at an opposite end to one end of a left side frame member 30b. Opposite ends of the right side weigh frame member 30a and the left side weigh frame member 30b are mounted to a foot end frame member 30d. A middle weigh frame member 30e is mounted at opposite ends to the right and left side weigh frame members 30a and 30b respectively between the head end and foot end frame members 30c and 30d. The frame member 32a is shown mounted between the right side frame member 30a and the mattress support frame 34, and the frame member 32b is shown mounted between the left side frame member 30b and the mattress support frame 34. It will be understood that other structural support is provided between the weigh frame 30 and the mattress support frame 34.

A right head load cell (RHLC) 50a is shown as positioned near the right head end of the patient support apparatus 10 between a base support frame 44a secured to the base 44 near the head end 46 of the patient support apparatus 10 and the junction of the head end frame member 30c and the right side frame member 30a, as shown in the block diagram of FIG. 3. A left head load cell (LHLC) 50b is shown as positioned near the left head end of the patient support apparatus 10 between the base support frame 44a and the junction of the head end frame member 30c and the left side frame member 30b, as shown in the block diagram of FIG. 3. A right foot load cell (RFLC) 50c is shown as positioned near the right foot end of the patient support apparatus 10 between a base support frame 44b secured to the base 44 near the foot end 48 of the patient support apparatus 10 and the junction of the foot end frame member 30d and the right side frame member 30a, as shown in the block diagram of FIG. 3. A left foot load cell (LFLC) 50d is shown as positioned near the left foot end of the patient support apparatus 10 between the base support frame 44b and the junction of the foot end frame member 30d and the left side frame member 30b. In the embodiment shown in FIG. 3, the four corners of the mattress support frame 34 are shown extending beyond the four corners of the weigh frame 30, and hence beyond the positions of the four load cells 50a-50d.

A weight distribution of a load among the plurality of load cells 50a-50d may not be the same depending on sensitivities of each of load cells 50a-50d and a position of the load on the patient support surface 36. Accordingly, a calibration constant for each of the load cells 50a-50d is established to adjust for differences in the load cells 50a-50d in response to the load. Each of the load cells 50a-50d produces a signal indicative of the load supported by that load cell 50. The loads detected by each of the respective load cells 50a-50d are adjusted using a corresponding calibration constant for the respective load cell 50a-50d. The adjusted loads are then combined to establish the actual weight supported on the patient support apparatus 10.

To determine a set of calibration constants, a calibration weight is sequentially placed on each of several predetermined calibration positions 70 on the patient support surface 36. For example, when determining a set of initial calibration constants, the calibration positions 70a, 70b, 70c, and 70d corresponding to the location of the load cells 50a, 50b, 50c, and 50d, respectively, are used. The calibration weight has an established mass which is used to determine the calibration constants. The respective initial calibration constants are determined by placing the calibration weight on a first calibration position 70a and measuring the weight distribution of the predefined calibration weight on each of the respective load cells 50a-50d. The respective loads detected by each of the load cells 50a-50d that corresponds to the current distribution of the predefined calibration weight on the first calibration position 70a is established and stored in the local RAM unit 66. The predefined calibration weight is then moved to the next calibration position 70b and the measuring and storing steps are repeated until a set of load weights are established for each of the respective calibration positions 70a-70d.

The plurality sets of load weights that correspond to the location of each load cell 50a-50d are used to generate the calibration equations (1)-(4) set forth below.

$$CWRH = C_1L_1 + C_2L_2 + C_3L_3 + C_4L_4 \quad (1)$$

$$CWLH = C_1L_1 + C_2L_2 + C_3L_3 + C_4L_4 \quad (2)$$

$$CWRF = C_1L_1 + C_2L_2 + C_3L_3 + C_4L_4 \quad (3)$$

$$CWLF = C_1L_1 + C_2L_2 + C_3L_3 + C_4L_4 \quad (4)$$

where CWRH, CWRF, CWLF, and CWLH are the predefined calibration weight when the predefined calibration weight is positioned on the calibration positions 70a-70d which correspond to the RHLC 50a, RFLC 50b, LFLC 50c, and LHLC 50d, respectively, C1, C2, C3, and C4 are calibration constants for RHLC 50a, RFLC 50b, LFLC 50c, and LHLC 50d, respectively, and L1, L2, L3, and L4 are the load weights on RHLC 50a, RFLC 50b, LFLC 50c, and LHLC 50d, respectively. CWRH, CWRF, CWLF, and CWLH are all equal to the predefined calibration weight. Thus, the initial calibration constants C1, C2, C3, and C4 are established using a standard Gauss-Jordan or other appropriate elimination method and equations (1)-(4) are solved to obtain values for initial calibration constants C1, C2, C3, and C4. The initial calibration constants C1, C2, C3, and C4 are applied to the loads detected by the respective load cells 50a-50d is used to determine the total weight supported on the load cells 50a-50d. It should be appreciated that the calibration constants may be dynamically refined based on the position and/or weight of the load.

In some embodiments, the position of the patient is determined by calculating a locus of a centroid of the patient load. The centroid of the patient load is represented as a point relative to a reference position or a coordinate axis of the patient support apparatus 10. The point is a coordinate (X, Y) within a two-dimensional Cartesian coordinate system having two horizontally extending X and Y axes along the patient support surface 36. The determination of the centroid of the patient load is described in expired U.S. Pat. No. 5,276,432, which is incorporated by reference herein in its entirety for its disclosure of a patient load location determination approach.

Figure 4:
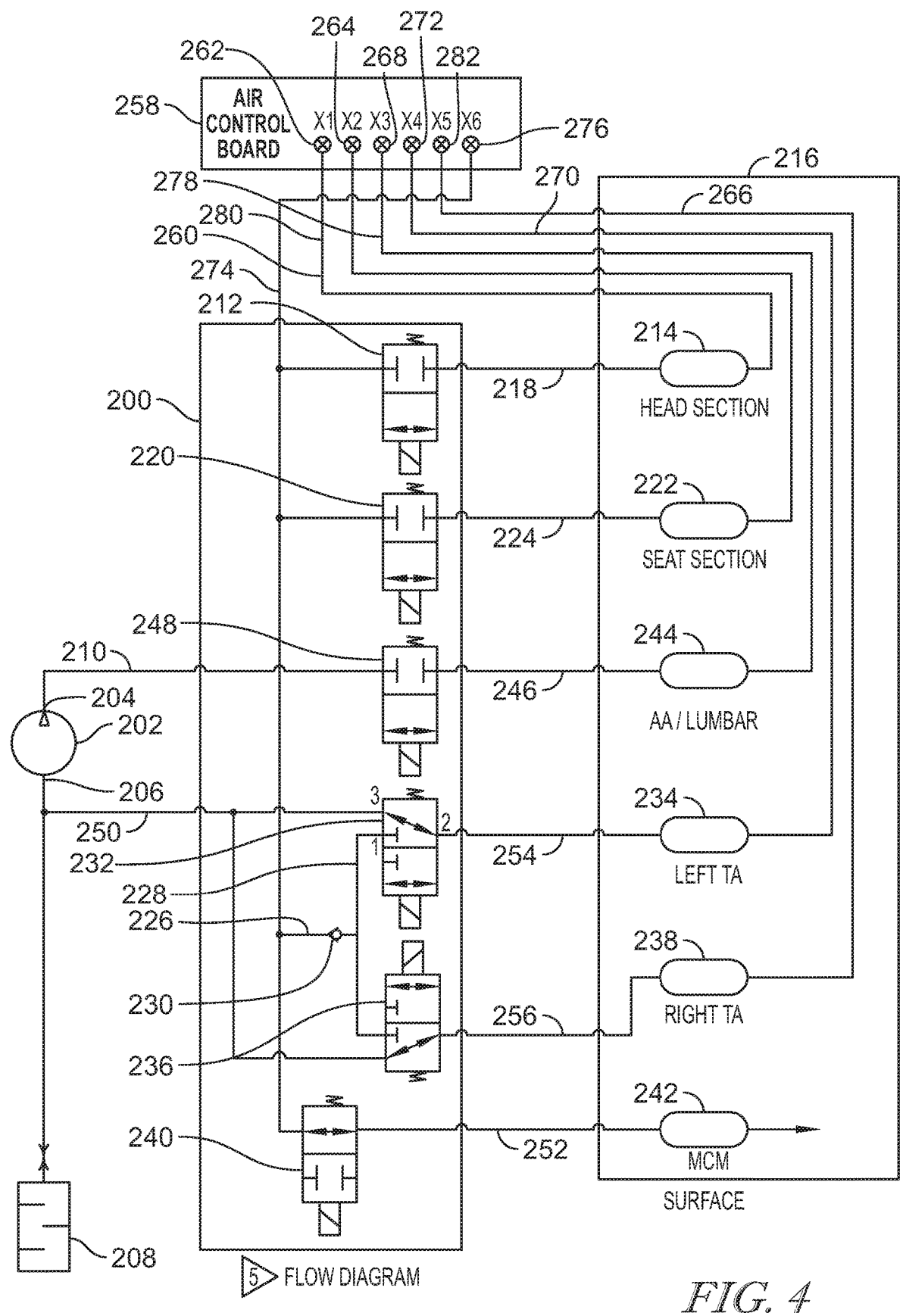
FIG. 4 is a schematic diagram of the pneumatics of an airbox assembly for the mattress shown in FIG. 1.

FIG. 4 is a diagrammatic representation of a pneumatic portion of an airbox for a mattress system 110 (shown in FIG. 8) that is positioned within the mattress 18. The details of the structure of a suitable pneumatic mattress may be found in application number PCT/US2016/34908 filed May 29, 2016 and having the title "PATIENT SUPPORT APPARATUS", which is incorporated herein in its entirety. In the embodiment of FIG. 4, the airbox includes a manifold 200 in a fluid communication with a blower 202, the blower having a positive pressure outlet 204 and a negative pressure inlet 206. In addition, the airbox includes a filter 208 through which air is drawn to the negative pressure inlet 206. The positive pressure outlet 204 feeds a conduit 210. The conduit 210 feeds a first valve 212 that controls flow to and from the head zone 214 of the body support 216 through the supply tube 218. A second valve 220 controls the flow to and from the seat zone 222 through the supply tube 224. Both of the valves 212 and 220 are movable between an opened and a closed position to connect the respective zones 214 and 222 to the conduit 210 as necessary. The conduit 210 also feeds a tap 226 that is connected to a conduit 228 through a check valve 230. When the pressure in the conduit 210 is of sufficient pressure to overcome the check valve 230, the check valve 230 will open and allow flow to the conduit 228 which feeds two valves 232, associated with the left turn zone 234, and 236, associated with right turn zone 238. In addition, conduit 210 is connected to a valve 240 which is associated with the microclimate management structure 242.

In some embodiments, the body support 216 includes an additional lumbar zone 244. The zone 244 is fed by a tube 246 from a valve 248 which is connected to the conduit 210. Another conduit 250 is connected to a second port on each of the turn valves 232, 236 and is connected to the inlet 206 of the blower 202. As will be described in further detail, each of the zones 214, 222, 234, 238, 244 may be exhausted through the valve 240, with the turn zones 234, 238 being subjected to a rapid evacuation through the use of the negative pressure inlet 206 of the blower 202 to draw air from the zones 234, 238 through the respective valves 232, 236

The zones 214, 222 may be vented through the valve 240 and microclimate management structure 242 if the blower 202 is idle such that the pressure in the conduit 210 is lower than the pressure in the zones 214 and 222. Opening of the valve 240 permits air from the zones 214 and 222 to flow through the conduit 210 through the valve 240 and inlet tube 252 to escape through the microclimate management structure 242.

Venting of the turn zones 234, 238 utilizes the three-way valve structure of valves 232, 236 to connect the respective feed tubes 254 or 256 to the conduit 250 so that the inlet side of the blower 202 pulls air through the conduits 266, 256 into the conduit 250 and, thereby, the inlet 206 of the blower 202. In certain conditions, the valves 232 or 236 may be positioned to allow air to be drawn from the respective zone 234 or 238 into the inlet 206 of the blower 202 and fed to one of the other zones 214 or 222. However, if no flow is needed to either the zones 214 or 222, the flow from the turn zones 234 or 238 is simply exhausted through the valve 240 to the microclimate management structure 242. As described in the aforementioned application number PCT/US2016/34908, under certain conditions, the pressure in the turn zones 234, 238 may exceed the pressure in another zone, such as the other turn zone 234 or 238, or the head zone 214 or seat zone 222. This may be a result of the weight of a patient and the leverage provided by Z-plate assemblies to urge their out of the bladder assemblies. To protect against damage to a body support, both the head zone 214 and seat zone 222 include a respective check valve positioned on a bottom surface of a lower layer. The check valves open at a relief pressure that is higher than the maximum operating pressure of the body support, but lower than the pressure which components of the body support would fail due to excessive pressure. While the turn zones operate at pressures higher than the typical operating pressures of the body support, the presence of the check valves mitigate the potential for a damaging overpressure condition to occur if the turn zones are vented through the microclimate management system 242 and the flow is constricted sufficiently to cause an overpressure condition in the body support.

An air control board 258 includes logic that is operable to take pressure readings from the manifold 200 or any one of the zones 214, 222, 234, 238, or 244 to determine which of the valves 212, 220, 232, 236, or 240 to open or adjust to achieve the flow necessary to meet the operational requirements of the body support 216. As described above, the head zone 214 is connected to a sense tube 260 which connects to a pressure sensor 262, the pressure sensor 262 providing a signal to the logic of the air control board 258 indicative of the pressure in the head zone 214. Similarly, the sense line 280 is connected to a pressure transducer 264 which provides a signal to the logic indicative of the pressure in the seat zone 222. The sense tube 266 provides a signal to a pressure transducer 282 indicative of the pressure in the right turn zone 238 and the sense tube 270 is connected to a pressure transducer 272 for determining the pressure in the left turn zone 234. The conduit 210 is coupled to a sense line 274 that is also connected to a pressure transducer 276, the pressure transducer 276 providing the logic a signal indicative of the pressure in the conduit 210. A sense line 278 connects the zone 244 to a pressure transducer 268 on the air can control board 258.

Figure 5:
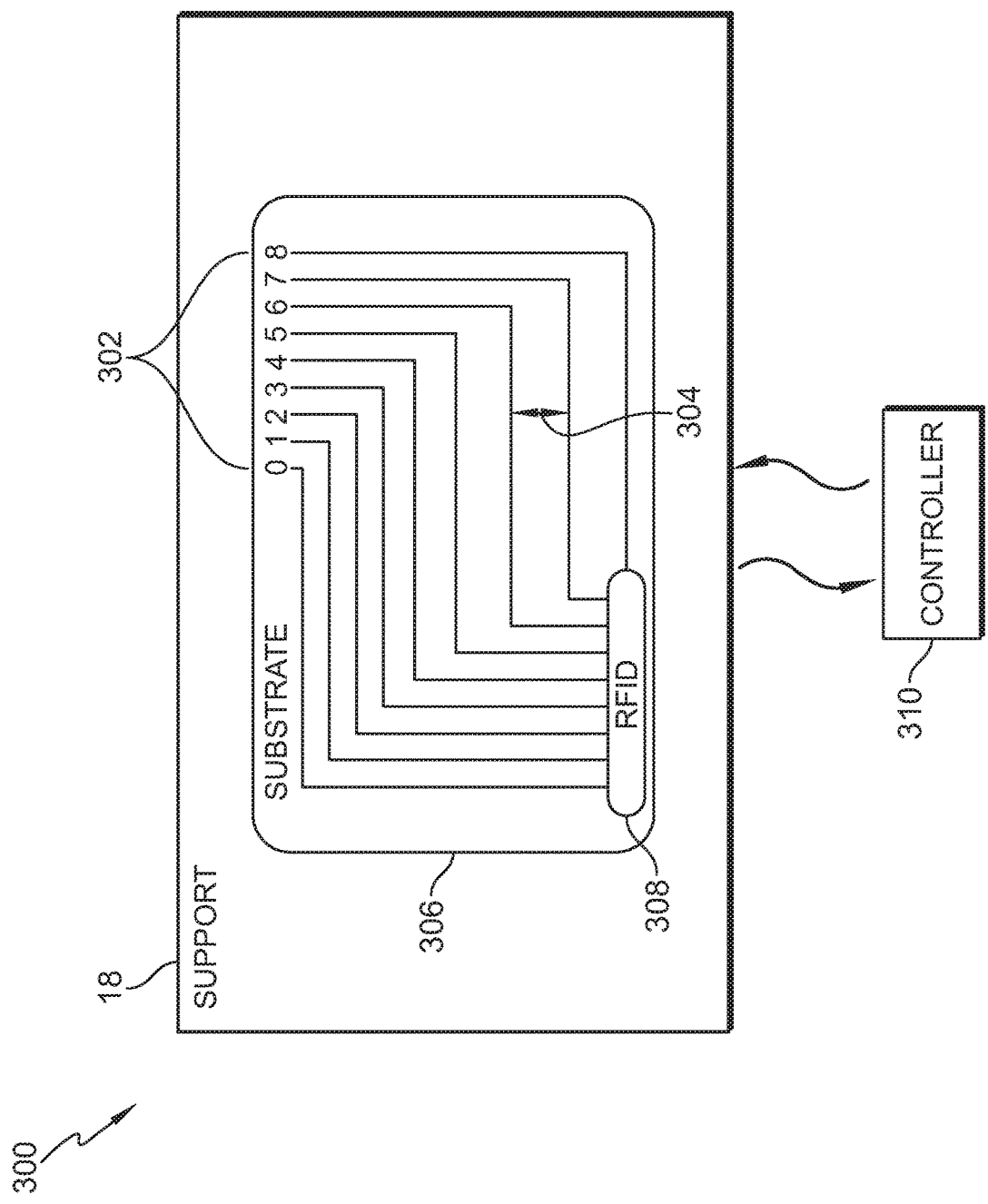
FIG. 5 is a schematic view of an embodiment of a sensor pad for detecting moisture presence and moisture volume.
Figure 6:
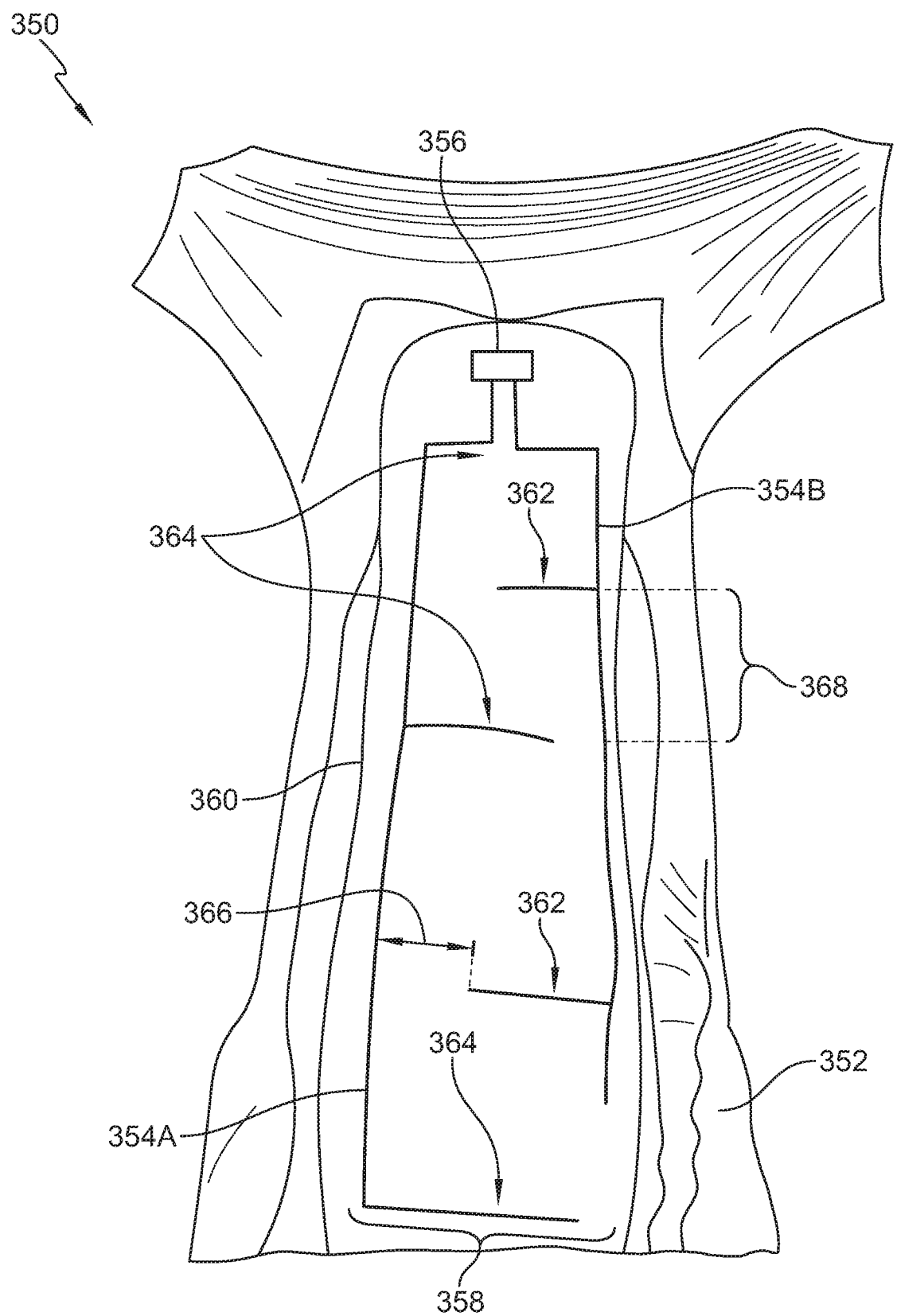
FIG. 6 is a plan view of a wearable sensor pad for detecting moisture presence above a minimum volume.
Figure 7:
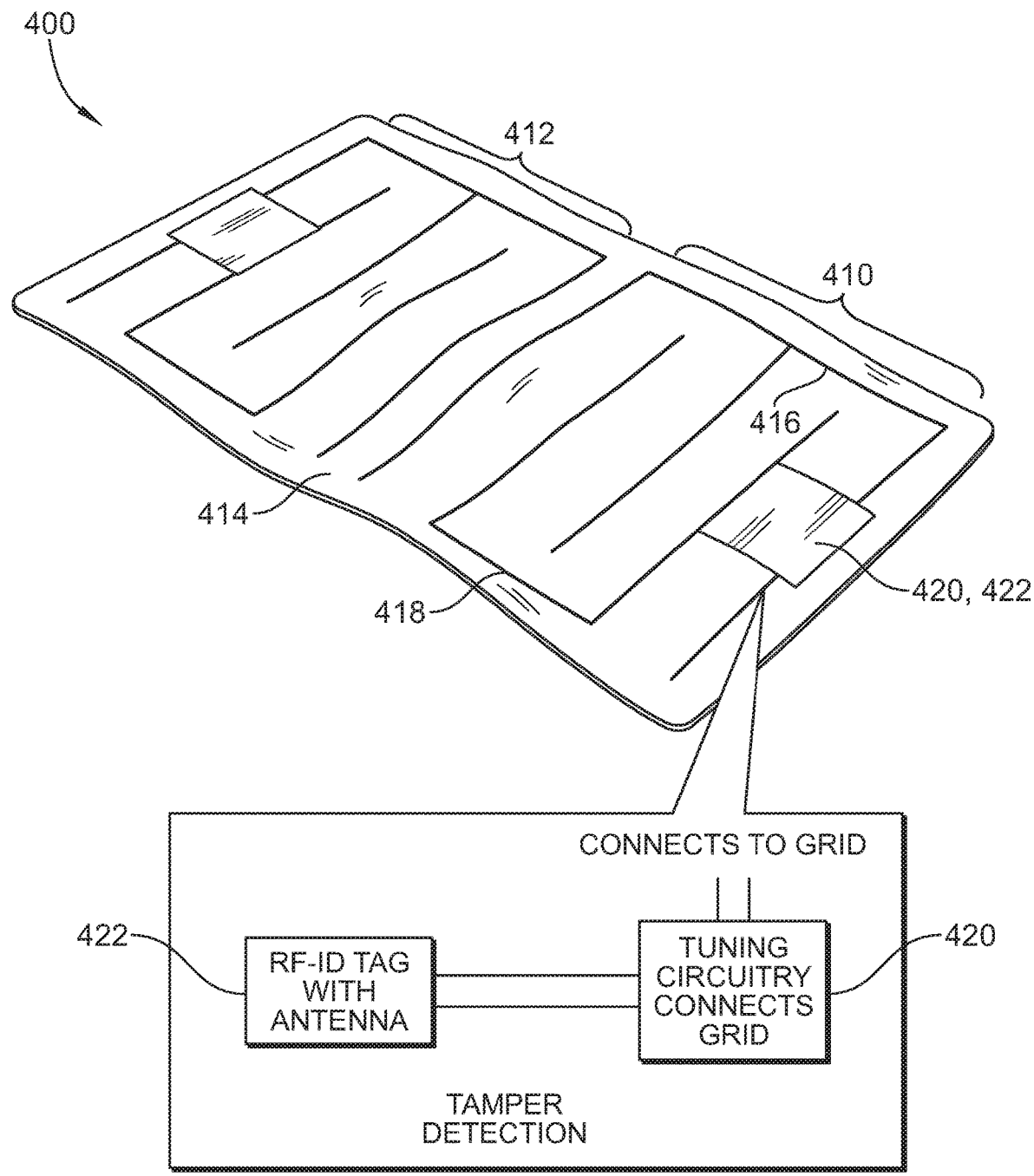
FIG. 7 is a perspective view of an embodiment of a sensor pad for detecting moisture presence above a minimum volume showing two RFID sensors each connected to a respective sensor trace grid.

FIGS. 5-7 schematically show two embodiments of a sensor system 300, 350 that detects a volume of incontinence or other moisture. The details of an incontinence sensor system of a patient support apparatus may be found in PCT/US2016/62167 filed Nov. 16, 2016 and having the title "INCONTINENCE DETECTION SYSTEMS FOR HOSPITAL BEDS," which is incorporated herein in its entirety. Sensor system 300 is shown in FIG. 5, which shows a substrate, or incontinence pad 306, resting on the mattress 18, in an area or zone in which it is desired to conduct surveillance for unwanted moisture or other moisture related abnormalities. In other embodiments, the pad 306 is integrated into the mattress 18. In still other embodiments, the pad 306 is integrated within an undergarment or other article of clothing or the pad 306 itself is a diaper or disposable undergarment. In other embodiments, the pad 306 is integrated into any patient support apparatus.

The system 300 for detecting a volume of moisture on the mattress 18 includes a plurality of sensor traces 302. The plurality of sensor traces 302 in the embodiment of FIG. 5 includes sensing traces 0-8. It is contemplated that there are more or fewer sensor traces in other embodiments. The sensor traces are placed at predetermined distances 304 from one another and portions or segments of the traces lie in parallel. It should be understood, however, that while the segments (e.g., 0, 1, 2, 3, 4, 5, 6, 7 and 8) are shown in FIG. 5 as linear segments, any suitable spatial arrangement of the sensing traces 302 that maintains the desired spacing 304 between the sensing traces 302 work sufficiently according to this disclosure.

In one embodiment, sensor traces 0-7 are generally Z-shaped, each with a first end segment coupled to an RFID tag 308, a second end segment spaced from the first segment and generally parallel therewith, and a middle segment interconnecting the end segments and oriented in substantially perpendicular relation with the end segments. The first segments of traces 0-7 are of decreasing length from trace 0 (i.e., the longest first segment) to trace 7 (i.e., the shortest first segment). The second segments of traces 0-7 are of increasing length from trace 0 (i.e., the shortest second segment) to trace 7 (i.e., the longest second segment). The middle segments of each trace 0-7 is approximately the same length as each of the other middle segments of each of the other traces 0-7. Trace 8 is generally L-shaped in the embodiment of FIG. 5, having a first segment coupled to the RFID circuit in substantially parallel relation with the middle segments of traces 0-7 and a second segment that is substantially perpendicular to the first segment of trace 8 and substantially parallel with the first and second end segments of traces 0-7. The length of the first segment of trace 8 is approximately equal to the lengths of the middle segments of traces 0-7.

In some embodiments, the distance 304 between each of the adjacent traces 0-8 is the same for each segment of each trace 0-8. In other embodiments, the distance 304 between each of the sensor traces 0-8 is different. It is also contemplated by this disclosure that, in some embodiments, the distance 304 between middle segments of traces 0-7 and between the middle segment of trace 7 and the first segment of trace 8 is different than the distance 304 between respective first end segments of traces 0-7, respective second end segments of traces 0-7, and the second segment of trace 8 and the second end segment of trace 7 of other traces. The distance 304 between each sensor trace is defined by one or more moisture management criteria, for example.

The moisture management criterion includes a moisture-related property of the substrate pad 306 in some instances. For example, a moisture management criterion may be a moisture-related property of the moisture absorbent material of the incontinence pad (such as, for example, a wicking or absorption property).

In one embodiment, the distance 304 is in the range of about 4 inches, based on a desired moisture sensitivity in the range of about 50 milliliters (e.g., 304 is the distance that 50 ml of liquid travels in the specified type of material forming the substrate 306 or a layer of an incontinence pad in which the substrate 306 is integrated). Thus, a notification is issued by a notification device as described elsewhere herein, when the sensor traces 6-7 are exposed to moisture indicating an amount of moisture in the range of about 50 milliliters (i.e., enough moisture to bridge two adjacent traces 302). In another embodiment, if moisture is exposed to sensing traces 6, 7, 8, a signal is generated indicating an amount of moisture in the range of 100 milliliters (i.e., enough moisture to bridge three adjacent traces 302). Likewise, if sensing traces 5, 6, 7, 8 are exposed to moisture, a signal is generated indicating an amount of moisture in the range of 150 milliliters (i.e., enough moisture to bridge four adjacent traces). Thus, system 300 is a high resolution incontinence detection system in that it is able to determine how much biofluid is being sensed by traces 302. The sensor traces 302 are connected to a passive RFID tag 308 in the embodiment of FIG. 5. RFID tag 308 is excited by a controller 310 which transmits an electromagnetic signal and receives the response from the RFID tag 308.

Referring now to FIG. 6, system 350 is incorporated into a wearable substrate such as a diaper or other wearable pad 352. In this embodiment, connector traces 354A, 354B extend from passive RFID tag 356 and extend longitudinally in substantially parallel relation along the outer edges of a moisture zone 358 of the diaper or wearable pad 352. Shielding material or a shield 360 coat or otherwise overlie each of the connector traces 354A, 354B to prevent the connector traces from being exposed to moisture. Alternatively or additionally, connector traces 354A, 354B lie outside moisture zone 358 in some embodiments so as to inhibit any chance for exposure to moisture that is present within zone 358. In some embodiments therefore, shields 360 are not needed for covering traces 354A, 65-4B and are omitted.

First and second sets of sensor traces 362, 364 extend from respective connector traces 354A, 354B in a direction substantially perpendicular to traces 354A, 354B. Traces 362, 364 extend across the moisture zone 358 but terminate prior to reaching the opposite trace 354A, 354B. Thus, in one embodiment, traces 362 each extend from trace 354B and terminal ends of traces 362 are spaced from trace 354A. Similarly, traces 364 each extend from trace 354A and terminal ends of traces 364 are spaced from trace 354B. A distance 366 (shown in FIG. 6 between the terminal end of one of traces 362 and trace 354A) is provided between each terminal end of traces 362, 364 and the trace 354A, 354B spaced therefrom.

The first 362 and second traces 364 are arranged in an alternating pattern along the length of the diaper 352. Thus, trace 354 and its accompany traces 364 form a first comb-like pattern and trace 362 and its accompanying traces 362 form a second comb-like pattern. The comb-like patterns are arranged to that traces 362 are interdigitated with traces 364. The spacing distance 366 is smaller than a spacing 368 between adjacent traces 362, 364. Because of the shielding 360 covering traces 354A, 354B, moisture that would otherwise make an electrical connection between terminal ends of traces 362, 364 and the traces 354A, 354B spaced therefrom by distance 366, is unable to do so. Instead, an electrical connection is made between only when sufficient moisture is present to expose a first and second sensor trace 362, 364 to moisture across distance 368. For example, in some embodiments contemplated herein, distance 368 between first and second sensor traces 362, 364 requires that 150 milliliters (ml) of moisture be present within moisture zone 358 before an electrical connection is made between adjacent traces 362, 364. Thus, the distance 368 is selected in the one embodiment so that a signal from RFID tag 356 is generated in response to moisture contacting one first sensing trace 362 and one second sensing trace 364 which occurs when about 150 milliliters (ml) of moisture is present in the moisture zone 358.

By shielding connecting traces 354A, 354B with moisture resistant layers (not shown) that comprise shields 360, oversensitivity may be avoided such that a signal may only be generated when a prescribed fluid volume is present in the moisture zone 358. This prevents, for example, incontinence signals being sent by RFID tag 356 in response to perspiration or other moisture that bridges across any of spaces 366. Alternatively, connecting traces 354A, 354B are positioned outside of moisture zone 358 as mentioned above to achieve a similar result. The first sensing traces 362 and second sensing traces 364 are spaced apart by a predetermined distance 368 that is based on a desired moisture sensitivity which also takes into account the wicking and absorbency properties of the diaper or other wearable pad 352 within zone 358. According to the present disclosure, shielded connector traces, similar to traces 354A, 354B, and unshielded sensor traces, similar to traces 362, 364, also may be used in non-wearable pad embodiments, such each of the other pad embodiments disclosed herein.

FIG. 7 discloses another embodiment of an RFID implemented moisture detection sensor system 400 employing a pair of sensors 410, 412 on a substrate such as a patient support or pad 414. The discussion below of sensor 410 is equally applicable to sensor 412. That is sensor 410 and sensor 412 are substantially the same although, in one embodiment, sensor 412 is a mirror image of sensor 410. Sensor 410 includes first and second trace grids 416, 418 that are spaced apart and form a somewhat serpentine pattern on the bed. Trace 418 is generally U-shaped and trace 416 is generally M-shaped or W-shaped depending upon the direction at which trace 416 is viewed. The U-shaped pattern of trace 418 is interdigitated with the M-shaped pattern of trace 416. Thus, traces 416, 418 form a comb-like pattern. Moisture detection takes place at the sensor 410 by way of a tuning circuit 420 connected to an RFID tag 422. When moisture bridges any of the spaces between trace 416 and trace 418, tuning circuitry 420 outputs a signal to RFID tag 422 which, in turn, emits a wireless signal indicating that moisture is present.

Figure 9B:
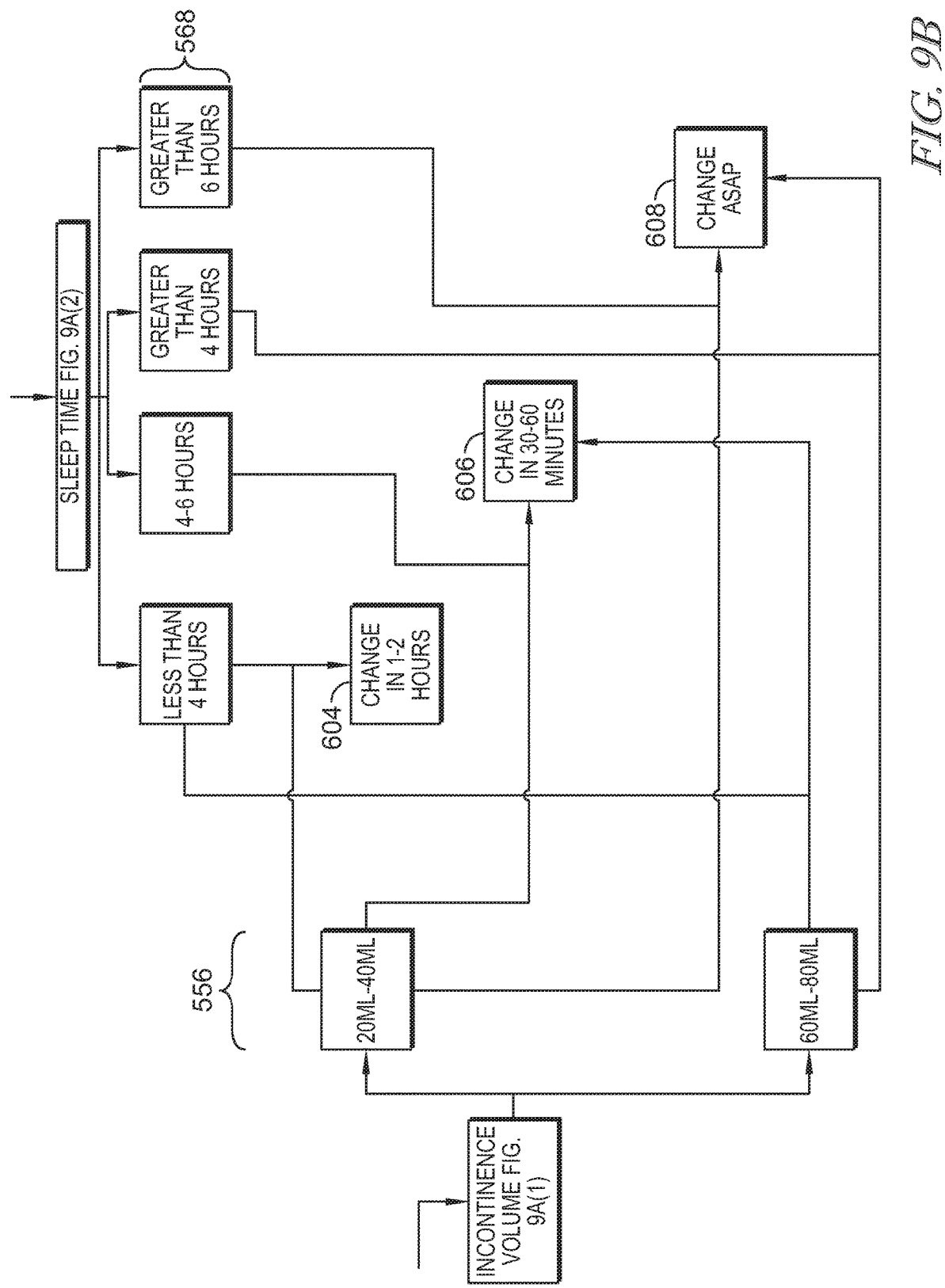
FIG. 9B is a continuation of the flowchart of FIG. 9A showing a method for determining a hygiene services schedule for a patient.

FIG. 8 is a block diagram of a system 500 which includes multiple components of the patient support apparatus 10 that cooperate to determine a hygiene services schedule for a patient supported on the patient support apparatus 10. In one embodiment, hygiene services for the patient may include changing the patient's linens, changing the patient's garments, and/or moving the patient to a clean hospital bed, among other things. A method, as shown in the flowchart of FIG. 9A-9B is executed by the system 500. The vital signs monitoring system 108 receives and transmits data to a sleep status calculator 504. For example, the data may represent brain activity, cardiac, respiratory, and/or snoring state of a patient. This data is transmitted to the sleep status calculator 504, where the data is analyzed along with data from the weigh scale system 60 and the mattress system 110. The data from the weigh scale system 60 and/or the mattress system 110 may represent movement of the patient, time that the patient is still, and/or bed exit data, among other things. The sleep status calculator 504 includes a processor 506 and a memory 508 to analyze and compare the data from the vital signs monitoring system 108, the weigh scale system 60, and the mattress system 110. The processor 506 may include a microprocessor-based controller having a flash memory unit and a local random-access memory (RAM) unit. The memory 508 may store data related to incontinence events, sleep history, and/or sleep patterns. Additionally, these data are compared to data from the sensor system 300, 350 to determine a hygiene services schedule for a patient. This schedule is displayed on a graphical user interface (GUI) 510 or similar device.

Referring to FIGS. 9A-9B, determining the hygiene services schedule includes the detection and measurement of incontinence of the patient. At step 550, the sensor system 300, 350 detects the occurrence of an incontinent event and then, at step 552, determines a type of incontinence, i.e. urine or fecal matter. If the type of incontinence contains fecal matter 553, at an alert is sent to the GUI 510 indicating that the patient should receive hygiene services as soon as possible 555, regardless of whether the patient is awake or asleep. It should be appreciated, that the terminology as soon as possible, is known to mean either immediately or upon the first available opportunity. If the type of incontinence contains urine 557, at step 554, a volume of the urine is determined by the sensor system 300, 350. In one embodiment, the volume of the urine may be categorized into various ranges (i.e. 0 ml-10 ml, 10 ml-20 ml, 20 ml-40 ml, 60 ml-80 ml, or greater than 80 ml). These ranges are referenced as 556 in FIG. 10, which shows a chart for determining the hygiene services schedule. It should be noted that one of ordinary skill in the art would recognize that any number of ranges representing any volumes of incontinence are contemplated by this disclosure. It should also be recognized that the shown ranges are contemplated to be approximate.

Determining the hygiene services schedule also includes determining a sleep status of the patient. Particularly, data from the vital signs monitoring system 108, the weigh scale system 60, and the mattress system 110 may be processed and analyzed by the sleep status calculator 504 to determine whether a patient is sleeping or awake. The data may also be utilized to determine an amount of time that the patient has been sleeping. For example, vital signs such as brain activity, heart rate, and/or respiratory rate may be indicative of a patient's sleep patterns. This data, in one embodiment, may be processed and analyzed to determine the occurrence of non-rapid eye movement (NREM) or rapid eye movement (REM) sleep. Additionally, patient movement data in the form of weight and/or pressure measurements from the weigh scale system 60 or mattress system 110 may provide evidence of sleeping, movement, and/or restlessness. Particularly, movement of the patient results in changes to the weight measured by the weigh scale system 60 and/or the pressure measured by the mattress system 110, thereby indicating patient movement, which may be attributed to restlessness, or lack of patient movement, which may be attributed to patient sleep. Moreover, the weigh scale system 60 or mattress system 110 may detect that the patient has left the patient support apparatus 10, thereby indicating that the patient is awake. This data may be utilized to determine whether the patient if awake or asleep and, if asleep, how long the patient has been sleeping. The length of time that a patient has been sleeping factors into the hygiene services schedule because it may be undesirable to wake a patient for hygiene services in certain circumstances.

At step 558, one or more vital signs are detected by the vital signs monitoring system 108. Concurrently, patient movement is detected by the weigh scale system 60, at step 560. Based on the data from the vital signs monitoring system 108 and the weigh scale system 60, the sleep status calculator 504 determines, at step 562, whether the patient is awake or asleep. If the patient is awake 563, hygiene services are scheduled to be provided as soon as possible at the occurrence of any incontinence event, at step 564. If the patient is determined to be asleep 565, the sleep status calculator 504 determines a time period that the patient has been asleep, at step 566. In one embodiment, the time period that the patient has been asleep may be categorized into various ranges (i.e. less than four hours, greater than four hours, between four hours and six hours, or greater than six hours). These ranges are referenced as 568 in chart in FIG. 10. It should be noted that one of ordinary skill in the art would recognize that any number of ranges representing any time period are contemplated by this disclosure. It should also be recognized that the shown time periods are contemplated to be approximate.

The sleep status calculator 504 determines a hygiene services schedule for the patient based on an approximate time that the patient has been sleeping and an approximate volume of biofluid from the incontinence event. The time that the patient has been sleeping may be compared to the approximate volume of the incontinence event to determine the hygiene services schedule. The hygiene services schedule provides an estimated time that within which the hygiene services should be provided. This schedule may be displayed on the GUI 510 and/or otherwise conveyed to the health care provider. FIG. 10 shows a plurality of exemplary hygiene services schedules based on exemplary sleep statuses and incontinence volumes. These schedules are referenced as 572 in FIG. 10. It should be noted that these schedules are exemplary and that alternatives schedules are contemplated by this disclosure.

In one embodiment, if the patient is asleep and the fluid volume of incontinence is within a range of approximately 0 ml to approximately 10 ml, hygiene services are not provided regardless of how long the patient has been asleep, at 600 (as shown in FIG. 9A). In another embodiment, if the patient is asleep and the fluid volume of incontinence is within a range of approximately 10 ml to approximately 20 ml, the time period to provide hygiene services is within a range of approximately 1 hour to approximately 2 hours regardless of how long the patient has been asleep, at 602 (as shown in FIG. 9A). In a further embodiment, if the patient has been asleep for less than approximately four hours and the fluid volume of incontinence is within a range of approximately 20 ml to approximately 40 ml, the time period to provide hygiene services is within a range of approximately 1 hour to approximately 2 hours, at 604 (as shown in FIG. 9B). In yet another embodiment, if the patient has been asleep for a range of approximately four hours to approximately six hours and the fluid volume of incontinence is within a range of approximately 20 ml to approximately 40 ml, the time period to provide hygiene services is within a range of approximately 30 minutes to approximately 1 hour, at 606 (as shown in FIG. 9B). In still another embodiment, if the patient has been asleep for over approximately six hours and the fluid volume of incontinence is within a range of approximately 20 ml to approximately 40 ml, the time period to provide hygiene services is as soon as possible, at 608 (as shown in FIG. 9B). In still yet another embodiment, if the patient has been asleep for less than approximately four hours and the fluid volume of incontinence is within a range of approximately 60 ml to approximately 80 ml, the time period to provide hygiene services is approximately 30 minutes to approximately 1 hour, at 606 (as shown in FIG. 9B). In a further embodiment, if the patient has been asleep for over approximately four hours and the fluid volume of incontinence is within a range of approximately 60 ml to approximately 80 ml, the time period to provide hygiene services is as soon as possible, at 608 (as shown in FIG. 9B). In still further another embodiment, if the patient is asleep and the fluid volume of incontinence is greater than approximately 80 ml, the time period to provide hygiene services is as soon as possible, at 610 (as shown in FIG. 9A).

Some of the above embodiments may be described in terms of functional block components and various processing steps. Such functional blocks may be realized by any number of hardware and/or software components configured to perform the specified functions. For example, embodiments may employ various integrated circuit components, e.g., memory elements, processing elements, logic elements, look-up tables, and the like, which may carry out a variety of functions under the control of one or more processors, microprocessors or other control devices. Similarly, where the elements of the above embodiments are implemented using software programming or software elements the embodiments may be implemented with any programming or scripting language such as C, C++, Java, assembler, or the like, with the various algorithms being implemented with any combination of data structures, objects, processes, routines or other programming elements. Furthermore, the embodiments could employ any number of conventional techniques for electronics configuration, signal processing and/or control, data processing and the like. The word "mechanism" may be used broadly and is not limited to mechanical or physical embodiments, but can include software routines in conjunction with processors, etc.

The particular implementations shown and described herein are illustrative examples and are not intended to otherwise limit the scope of the claims in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component disclosed herein is intended to be an essential element. Numerous modifications and adaptations will be readily apparent to those skilled in this art without departing from the spirit and scope of the embodiments.

Embodiments may be implemented with computer-executable instructions. The computer-executable instructions may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and/or described herein. Other embodiments may include different computer-executable instructions or components having more or less functionality than illustrated and described herein.

Although certain illustrative embodiments have been described in detail above, variations and modifications exist within the scope and spirit of this disclosure as described and as defined in the following claims.

The invention claimed is:

1. A patient monitoring system, comprising
a sensor system in a patient support apparatus including a first sensor operable to acquire sleep status data of a patient;
an incontinence detection system including a second replaceable sensor operable to detect incontinence status data of the patient;
a processor and a memory device, the memory device including instructions that, when executed by the processor, are operable to receive the patient sleep status data and the incontinence status data, process the patient sleep status data and the incontinence status data, and determine a recommended hygiene service based on the incontinence status data and the patient sleep status data; and
a display device controlled by the processor and operable to indicate to a caregiver at least one of the patient's incontinence status, the patient's sleep status, and the recommended hygiene service, wherein the recommended hygiene service, including replacement of the second sensor, is based on a fluid volume of incontinence detected by the second sensor and the sleep status of the patient;
wherein if the patient has been asleep for a first sleep period and the fluid volume of incontinence is within a first volume range, providing the recommended hygiene services after a first length of time, and if the patient has been asleep for a second sleep period that is longer than the first sleep period and if the fluid volume of incontinence is within the first volume range, providing the recommended hygiene services after a second length of time that is less than the first length of time, and if the patient has been asleep for the first sleep period and the fluid volume of incontinence is within a second volume range that is higher than the first volume range, providing the recommended hygiene services after a third length of time that is less than the first length of time.

2. The system of claim 1, wherein the display device is configured to display an indication in response to the determination of the recommended hygiene service.

3. The system of claim 1, wherein the first sensor comprises a patient movement sensor.

4. The system of claim 1, wherein the second sensor comprises a pad including a plurality of conductive traces.

5. The system of claim 1, wherein the display device is configured to indicate two or more of the patient's incontinence status, the patient's sleep status, and the recommended hygiene service.

6. The system of claim 1, wherein the first sensor is configured to acquire sleep status data of a patient includes a vital signs monitor and the determination of the sleep status of the patient is based on at least one vital sign.

7. The system of claim 6, wherein the vital signs monitor measures brain activity of the patient with an electroencephalogram.

8. The system of claim 6, wherein the vital signs monitor measures heart activity of the patient with an electrocardiogram.

9. A method of providing hygiene services to a patient positioned on a patient support apparatus, the method comprising:
acquiring at least one vital sign of a patient with a first sensor on the patient support apparatus;
acquiring incontinence event data based on a signal from a second replaceable sensor that is part of an incontinence detection system supported on a patient support apparatus;
after the occurrence of the incontinence event, determining a sleep status of the patient based on the at least one vital sign acquired from the first sensor;
automatically determining an acceptable length of time before providing hygiene services to the patient based on the incontinence event data from the second sensor and the sleep status of the patient acquired from the first sensor; and
automatically communicating the length of time before providing hygiene services is required to a caregiver, wherein the length of time before hygiene services, including replacement of the second sensor, is based on a fluid volume of incontinence detected by the second sensor and the sleep status of the patient;
wherein if the patient has been asleep for a first sleep period and the fluid volume of incontinence is within a first volume range, providing the recommended hygiene services after a first length of time, and if the patient has been asleep for a second sleep period that is longer than the first sleep period and if the fluid volume of incontinence is within the first volume range, providing the recommended hygiene services after a second length of time that is less than the first length of time, and if the patient has been asleep for the first sleep period and the fluid volume of incontinence is within a second volume range that is higher than the first volume range, providing the recommended hygiene services after a third length of time that is less than the first length of time.

10. The method of claim 9, wherein acquiring incontinence event data comprises detecting the incontinence event.

11. The method of claim 9, wherein measuring at least one vital sign comprises measuring brain activity of the patient with an electroencephalogram.

12. The method of claim 9, wherein measuring at least one vital sign comprises measuring heart activity of the patient with an electrocardiogram.

13. The method of claim 9, further comprising measuring movement of the patient and an acceptable length of time before providing hygiene services to the patient is based at least in part on the magnitude of movement of patient being measured.

14. The method of claim 13, wherein measuring movement of the patient further comprises measuring movement of the patient with a load cell.

15. The method of claim 9, wherein determining a sleep status includes determining a period of time that the patient has slept.

16. The method of claim 9, wherein, if the patient is asleep and the fluid volume is between a first predetermined volume and a second predetermined volume greater than the first predetermined volume, the acceptable length of time before providing hygiene services is between a first predetermined elapsed time and a second elapsed time, the second elapsed time greater than the first elapsed time.

17. A system for providing hygiene services to a patient, the system comprising:
- a first sensor in a patient support apparatus configured to acquire a vital sign of a patient;
- an incontinence detection system supported on the patient support apparatus, the incontinence detection system including a second replaceable sensor detecting incontinence event data;
- a processor operable to, after the occurrence of an incontinence event detected by the second sensor, determine a sleep status of the patient based on the vital sign from the first sensor of the patient support apparatus, the processor further configured to determine a time period to provide hygiene services to the patient based on the incontinence event data and the sleep status of the patient and convey the time period for hygiene services to a caregiver, the hygiene services including replacement of the second sensor is based on a fluid volume of incontinence detected by the second sensor and the vital sign of the patient;
- wherein if the patient has been asleep for a first sleep period and the fluid volume of incontinence is within a first volume range, providing the recommended hygiene services after a first length of time, and if the patient has been asleep for a second sleep period that is longer than the first sleep period and if the fluid volume of incontinence is within the first volume range, providing the recommended hygiene services after a second length of time that is less than the first length of time, and if the patient has been asleep for the first sleep period and the fluid volume of incontinence is within a second volume range that is higher than the first volume range, providing the recommended hygiene services after a third length of time that is less than the first length of time.

18. The system of claim 17, wherein the vital sign comprises heart activity of the patient measured with an electrocardiogram.

19. The system of claim 17, further comprising a display device configured to display an indication in response to the determination of the recommended hygiene service.

20. The system of claim 19, wherein the display device is configured to indicate two or more of the patient's incontinence status, the patient's sleep status, and the recommended hygiene service.

21. The system of claim 17, wherein the first sensor further comprises a patient movement sensor.

22. The system of claim 17, wherein the second replaceable sensor comprises a pad including a plurality of conductive traces.

23. The system of claim 17, wherein the first sensor is configured to acquire sleep status data and the determination of the sleep status of the patient is based on at least one vital sign.

24. The system of claim 23, wherein the first sensor monitor measures brain activity of the patient with an electroencephalogram.

25. The system of claim 23, wherein the first sensor monitor measures heart activity of the patient with an electrocardiogram.

* * * * *